United States Patent [19]

Kuwata et al.

[11] Patent Number: 5,871,761
[45] Date of Patent: Feb. 16, 1999

[54] METHOD FOR THE PREPARATION OF IMPROVED WATER-BASE TOILETRY COMPOSITION

[75] Inventors: Satoshi Kuwata; Morizo Nakazato; Yoshinori Inokuchi, all of Gunma-ken, Japan

[73] Assignee: Shin-Etsu Chemical Co., Ltd., Japan

[21] Appl. No.: 928,671

[22] Filed: Sep. 12, 1997

[30] Foreign Application Priority Data

Sep. 13, 1996 [JP] Japan .................................. 8-242854

[51] Int. Cl.$^6$ ............................. A61K 6/00; A61K 7/00; A61K 7/06
[52] U.S. Cl. .......................... 424/401; 424/70.1
[58] Field of Search ................. 424/401, 70.1, 424/70.12; 514/937

[56] References Cited

U.S. PATENT DOCUMENTS 4,749,732   6/1988   Kohl et al. ................................ 524/43

Primary Examiner—Thuman K. Page
Assistant Examiner—Sharon Howard
Attorney, Agent, or Firm—Miller, White, Zelano & Branigan, P.C.

[57] ABSTRACT

Proposed is a reliable method for the preparation of a water-base hair-care or skin-care toiletry preparation capable of imparting the hair or skin of the user with excellent touch feeling of smoothness and sleekness. The method comprises (a) preparing an aqueous dispersion of globular particles of a cured silicone rubber having a specified average particle diameter by the in situ crosslinking hydrosilation reaction in liquid droplets of a vinyl group-containing dimethylpolysiloxane and an organohydrogen-polysiloxane in combination in the presence of a surface active agent and (b) admixing a base mixture consisting of the principal ingredients of a water-base toiletry composition with a specified amount of the aqueous dispersion of the cured silicone rubber particles.

7 Claims, No Drawings

METHOD FOR THE PREPARATION OF IMPROVED WATER-BASE TOILETRY COMPOSITION

BACKGROUND OF THE INVENTION

The present invention relates to a method for the preparation of an improved water-base toiletry composition or, more particularly, to a method for the preparation of a hair-care or skin-care toiletry composition capable of imparting an excellent feeling of finishing to the hair or skin treated therewith.

The water-base toiletry compositions prepared according to the inventive method include hair-care preparations such as hair shampoos, hair rinses, hair treatments, hair conditioners, hair styling agents, hair perming agents, hair dyes and the like and skin-care preparations such as body shampoos, face creams, milky lotions, foundations, cleansing preparations and the like containing water as the solvent or dispersion medium.

It is a general requirement heretofore in the hair-care and skin-care toiletry preparations that the hair or skin treated therewith may have a feeling of smoothness or sleekness in touch. Namely, the hair after treatment with a hair-care preparation is desired to exhibit little resistance against combing and light and dry feeling of touch and the skin after treatment with a skin-care preparation is desired to have sleekness.

In this regard, various attempts and proposals have been made heretofore to improve a water-base hair-care or skin-care toiletry composition including admixture of a hair-care toiletry preparation with a cationic conditioning agent although the improvement accomplished thereby is limited. Besides, a proposal is made in Japanese Patent Kokai 61-210022, 2-247113, 4-327520 and 4-364113, Japanese Patent Publications 4-2566, 4-2567 and 4-38723 and elsewhere to admix a hair-care toiletry preparation with a non-volatile silicone oil. Another proposal is made in Japanese Patent Publication 7-29906 to formulate a hair-care toiletry preparation with a rigid silicone polymer and a further proposal is made in Japanese Patent Kokai 63-130512, 4-36226, 4-224309, 5-13994, 5-39212 and 5-163122 to formulate a hair-care toiletry preparation with a silicone oil in the form of an aqueous emulsion prepared separately. Although certain improvements can be obtained in the properties of the hair-care toiletry preparations prepared in accordance with the above mentioned proposals, the improvement is still limited and insufficient.

In respect of improving skin-care toiletry preparations and makeup compositions so as to be capable of imparting a pleasant touch feeling to the user's skin after treatment therewith, it is a current approach to admix the preparation with fine particles of a silicone or an organopolysiloxane. For example, Japanese Patent Kokai 1-265008 and 1-268615 propose to admix a skin-care toiletry composition with fine particles of an organosilsesquioxane resin. Japanese Patent Publication 4-17162 proposes addition of fine particles of a cured organopolysiloxane and Japanese Patent Publication 4-66446 proposes addition of a powder of an organopolysiloxane elastomer each to a skin-care toiletry preparation. Further, Japanese Patent Kokai 8-12545 and 8-12546 propose that an anti-perspirant and anti-suntan agent are compounded with fine spherical or globular particles of a cured silicone rubber. These prior art methods are, of course, not quite ineffective in improving the skin-care toiletry preparations to some extent though with a problem in respect of the dispersibility of the fine silicone particles into the base mixture of a skin-care toiletry preparation. This problem is particularly serious when the toiletry preparation is a water-base composition due to the inherently low hydrophilicity of silicone particles so that reproducible improvements can hardly be obtained thereby in the properties of the water-base skin-care toiletry preparations.

SUMMARY OF THE INVENTION

The present invention accordingly has an object, in view of the above described problems and disadvantages in the prior art water-base toiletry preparations for hair-care and skin-care treatments, to provide a novel and improved method with reproducibility for the preparation of a hair-care or skin-care toiletry preparation or composition capable of giving an improved hair or skin of the user exhibiting excellent touch feeling after treatment with the toiletry preparation even when the toiletry preparation is a water-base composition.

Thus, the method of the present invention for the preparation of an improved water-base toiletry preparation comprises the steps of:

(a) preparing an aqueous dispersion of spherical particles of a cured silicone rubber having an average particle diameter in the range from 0.1 to 100 $\mu$m or, preferably, from 1 to 10 $\mu$m dispersed in an aqueous medium containing a surface active agent, which is preferably a non-ionic surface active agent, the amount of the cured silicone rubber particles being in the range from 1 to 70% by weight, the amount of the surface active agent being in the range from 0.1 to 20% by weight and the balance being water, based on the amount of the aqueous dispersion; and (b) admixing a base mixture of a water-base toiletry preparation with the aqueous dispersion of the cured silicone rubber particles prepared in step (a) in such a proportion that the content of the cured silicone rubber particles in the toiletry preparation is in the range from 0.1 to 30% or, preferably, from 1 to 10% by weight based on the total amount of the non-volatile matters in the base mixture.

In particular, the aqueous dispersion of cured silicone rubber particles is prepared in step (a), preferably, by the method of in situ crosslinking reaction in a mixture consisting of an alkenyl-containing diorganopolysiloxane and an organohydrogenpolysiloxane jointly emulsified in an aqueous medium in the presence of a surface active agent by the mechanism of the hydrosilation reaction between the alkenyl groups in the alkenyl-containing diorganopolysiloxane and the silicon-bonded hydrogen atoms in the organohydrogenpolysiloxane in the presence of a platinum compound as a catalyst for the hydrosilation reaction.

DETAILED DESCRIPTION OF THE PREFERRED EMBODIMENTS

As is described above, the method of the present invention comprises the essential steps of (a) and (b), of which the step (a) is for the preparation of an aqueous dispersion of fine spherical or globular particles of a cured silicone rubber having a specified rubber hardness and a specified average particle diameter and the step (b) is for the admixture of the aqueous dispersion of the cured silicone rubber particles prepared in step (a) to a base mixture of the water-base toiletry preparation.

Although the process of step (a) for the preparation of an aqueous dispersion of cured silicone rubber particles is not particularly limitative, it is preferable that the aqueous dispersion of cured silicone rubber particles is prepared by the in situ crosslinking reaction taking place in fine droplets of a liquid organopolysiloxane precursor for a silicone rubber emulsified in an aqueous medium containing a surface active agent. The type of the crosslinking reaction between organopolysiloxane molecules is also not particularly limitative including the so-called hydrosilation reaction between silicon-bonded alkenyl groups and silicon-bonded hydrogen atoms promoted by a platinum catalyst and the condensation reaction between silicon-bonded hydroxyl groups and/or silicon-bonded alkoxy groups as well as the radiation-induced curing of an organopolysiloxane under irradiation with ultraviolet light or a high-energy radiation, of which the crosslinking reaction by the mechanism of hydrosilation is preferred.

In conducting the in situ crosslinking reaction to give cured silicone rubber particles by the mechanism of the hydrosilation reaction, a liquid precursor of a silicone rubber, which is a mixture or combination of an organopolysiloxane having at least two alkenyl groups bonded to the silicon atoms in a molecule and an organohydrogenpolysiloxane having at least two hydrogen atoms directly bonded to the silicon atoms in a molecule, is first emulsified in an aqueous medium containing a surface active agent as an emulsifier under agitation to form an aqueous emulsion, to which a catalytic amount of a platinum compound is added as a catalyst to promote the hydrosilation reaction so that the hydrosilation reaction proceeds at an elevated temperature or even at room temperature to convert the droplets of the liquid silicone rubber precursor into particles of a cured silicone rubber.

The alkenyl groups in the above mentioned alkenyl-containing organopolysiloxane can be vinyl groups or allyl groups, of which vinyl groups are preferred. The organic groups bonded to the silicon atoms in the alkenyl-containing diorganopolysiloxane other than the alkenyl groups are preferably monovalent hydrocarbon groups having 1 to 20 carbon atoms free from aliphatic unsaturation, optionally, substituted for all or a part of the hydrogen atoms in the hydrocarbon groups by halogen atoms. The organopolysiloxane should have at least two of the alkenyl groups in a molecule in order for the liquid silicone rubber precursor to be converted into a cured silicone rubber.

Examples of the unsubstituted or halogen-substituted monovalent hydrocarbon groups free from aliphatic unsaturation include: alkyl groups such as methyl, ethyl, propyl, butyl, pentyl, hexyl, heptyl, octyl, nonyl, decyl, dodecyl, tetradecyl, hexadecyl and octadecyl groups; aryl groups such as phenyl and tolyl groups; aralkyl groups such as 2-phenylethyl and 2-phenylpropyl groups; and halogen-substituted alkyl groups such as 3,3,3-trifluoropropyl, 2-(perfluoro-n-butyl) ethyl and 2-(perfluoro-n-octyl) ethyl groups. Although the monovalent hydrocarbon groups of a single kind or of two or more kinds in combination can be present in the alkenyl-containing organopolysiloxane, it is preferable that all or at least 90% by moles of the monovalent hydrocarbon groups other than alkenyl groups are methyl groups, the balance, if any, being phenyl groups.

The organohydrogenpolysiloxane to be combined with the above described alkenyl-containing organopolysiloxane to form a liquid silicone rubber precursor should have at least two hydrogen atoms directly bonded to the silicon atoms in a molecule. The organic groups bonded to the silicon atoms in the organohydrogenpolysiloxane molecules can be selected from the unsubstituted or halogen-substituted monovalent hydrocarbon groups free from aliphatic unsaturation as exemplified above relative to the alkenyl-containing organopolysiloxane. It is also preferable that all or at least 90% by moles of the monovalent hydrocarbon groups free from aliphatic unsaturation are methyl groups, the balance, if any, being phenyl groups. The blending proportion of the alkenyl group-containing diorganopolysiloxane and the organohydrogenpolysiloxane is such that the molar ratio of the alkenyl groups in the alkenyl group-containing diorganopolysiloxane to the silicon-bonded hydrogen atoms in the organohydrogenpolysiloxane is in the range from 0.8 to 1.2.

The crosslinking density in the cured silicone rubber particles is determined by the contents of the alkenyl groups in the alkenyl-containing organopolysiloxane and the silicon-bonded hydrogen atoms in the organohydrogenpolysiloxane, which must be appropriately selected so that the silicone rubber particles formed by the in situ crosslinking reaction may have a rubber hardness in the JIS A scale in the range from 10 to 90 or, preferably, from 20 to 80 as measured according to the procedure specified in JIS K 6301. When the hardness of the cured silicone rubber particles is too low, the toiletry preparation admixed with the aqueous dispersion of the cured silicone rubber particles can hardly be improved in respect of the sleek feeling of use while cured silicone rubber particles having a rubber hardness in the JIS A scale higher than 90 can hardly be obtained by the method of hydrosilation reaction in addition to the sandy feeling of use when such high-hardness silicone rubber particles are admixed in a water-base toiletry preparation.

Since it is a rather difficult or impossible matter to determine the rubber hardness of a fine silicone rubber particle by the JIS method, the above mentioned hardness of the cured silicone rubber particles refers to the value obtained by an alternative convenient method in which hardness measurement is performed for a cured silicone rubber sheet obtained with the same formulation and under the same curing conditions as those of the cured silicone rubber particles in an aqueous dispersion except that the liquid silicone rubber precursor is not emulsified in an aqueous medium.

It is a desirable condition that the configuration of the globular silicone rubber particles in the aqueous dispersion is as close to spherical as possible with an aspect ratio, i.e. the ratio of the longer axis to the shorter axis, not exceeding 1.2 or, more desirably, not exceeding 1.1.

In step (a) of the inventive method, the alkenyl group-containing organopolysiloxane and the organohydrogenpolysiloxane described above are, jointly as a mixture, first emulsified into fine droplets under agitation in an aqueous medium containing a surface active agent dissolved therein to serve as a silicone rubber precursor.

The surface active agent used here is not particularly limitative with regard to the ionic nature including non-ionic, anionic, cationic and amphoteric surface active agents provided that the surface active agent is compatible with the surface active agent contained in the base mixture of the hair-care and skin-care water-base toiletry preparations to which the aqueous dispersion of the silicone rubber particles is to be added.

Examples of the non-ionic surface active agent include polyoxyethylene alkylphenyl ethers, polyoxyethylene alkyl ethers, polyoxyethylene sorbitan fatty acid esters, glycerine fatty acid esters and the like having an HLB value in the range from 1.5 to 20 or, preferably, from 7 to 19. Examples of the anionic surface active agent include salts of alkyl sulfates, salts of alkylbenzene sulfonates, salts of dialkyl sulfosuccinates, salts of alkyl phosphoric acids, salts of polyoxyethylene alkyl ether sulfates, polyoxyethylene alkylphenyl ether sulfates and the like. Examples of the cationic surface active agent include long-chain alkyl trimethyl ammonium chlorides, alkylamine hydrochlorides, alkylamine acetates, long-chain alkyl phenyl dimethyl ammonium chlorides and the like. Examples of the amphoteric surface active agent include N-acylamidopropyl-N,N-dimethylammonio betaines, N-acylamidopropyl-N,N'-dimethyl-N'-2-hydroxypropylammonio betaines and the like. Among the above mentioned classes, the surface active agents belonging to the non-ionic surface active agents are preferred in most cases in respect of compatibility.

The amount of the surface active agent used in the preparation of the aqueous emulsion of the alkenyl-containing organopolysiloxane and organohydrogenpolysiloxane is not particularly limitative provided that stability of the emulsion can be ensured. As a rough measure, the amount of the surface active agent is in the range from 0.1 to 50% by weight or, preferably, from 0.5 to 30% by weight or, more preferably, from 1 to 10% by weight based on the total amount of the alkenyl group-containing organopolysiloxane and organohydrogenpolysiloxane. It should be noted that the amount of the surface active agent is determinative of the particle size distribution of the siloxane droplets and hence the average particle diameter of the cured silicone rubber particles, which must be in the range from 0.1 to 100 $\mu$m or, preferably, from 1 to 10 $\mu$m, so that the amount of the surface active agent should be selected depending on the desired average particle size of the silicone rubber particles. It should also be taken into account that the resultant aqueous dispersion of the cured silicone rubber particles to be added to a base mixture of a toiletry preparation contains from 1 to 70% by weight of the cured silicone rubber particles and from 0.1 to 20% by weight of the surface active agent, the balance being water and other minor ingredients, if any.

It is essential that the aqueous emulsion of the alkenyl group-containing organopolysiloxane and organohydrogenpolysiloxane as a mixture is admixed with a catalytic amount of a platinum compound in order that the hydrosilation reaction between the alkenyl groups and the silicon-bonded hydrogen atoms is promoted to convert the emulsified droplets into particles of a crosslinked silicone rubber. Suitable platinum compounds include chloroplatinic acid and complexes thereof with a vinyl siloxane or an olefin compound. When the aqueous emulsion of the siloxane mixture is admixed with the platinum catalyst and kept under agitation at room temperature or at an elevated temperature, for example, for 12 hours or longer, the droplets of the siloxane mixture are converted into particles of a cured silicone rubber as a consequence of the hydrosilation reaction to form crosslinks between the alkenyl group-containing organopolysiloxane and the organohydrogenpolysiloxane.

When step (a) of the inventive method is performed adequately in the above described manner, the cured silicone rubber particles in the aqueous dispersion have a substantially spherical or globular configuration of which the aspect ratio of the particles usually does not exceed 1.2 or, in most cases, does not exceed 1.1. The aspect ratio of a silicone rubber particle here implied is a parameter defined by the ratio of the length of the longest axis to the length of the shortest axis of the particle.

In step (b) of the inventive method to follow the step (a), the aqueous dispersion of cured silicone rubber particles prepared in the above described manner is added to and uniformly dispersed in a base mixture of a water-base hair-care or skin-care toiletry preparation. The water-base toiletry preparation here implied is a composition for toiletry applications which contains a substantial amount of water as a solvent or as a dispersing medium of other ingredients. The base mixture of the toiletry preparation is a mixture of principal ingredients of the composition which is admixed with the aqueous dispersion of the cured silicone rubber particles according to the inventive method. The essential requirement in the inventive method is that the cured silicone rubber particles are compounded with the base mixture consisting of the other ingredients of the toiletry preparations in the form of an aqueous dispersion as prepared in step (a) and not in the form of dried particles isolated from the aqueous dispersion medium. It is of course optional that the aqueous dispersion of the cured silicone rubber particles is blended with the ingredients to form the base mixture of the toiletry preparation altogether at one time. The amount of addition of the aqueous dispersion of the cured silicone rubber particles naturally depends on the types of the toiletry preparations and the preparation forms but it is usually in the range from 0.1 to 30% by weight or, preferably, from 1 to 10% by weight calculated as the particles of the cured silicone rubber based on the total amount of the non-volatile constituents in the base mixture of the toiletry preparation. When the amount of the silicone rubber particles is too small, the desired improvement can hardly be accomplished as a matter of course in respect of the sleek feeling which the user of the water-base toiletry preparation should obtain. When the amount of the cured silicone rubber particles is too large, the inherent role to be played by the water-base toiletry preparation may not be satisfactorily played or the stability of the water-base toiletry preparation is decreased.

The method of the present invention is applicable to any water-base toiletry preparations including hair-care toiletry preparations such as hair shampoos, hair rinses, hair treatments, hair conditioners, hair styling agents, hair perming agents, hair dyes and the like and to skin-care toiletry preparations such as body shampoos, face creams, milky lotions, foundations, face cleansing agents, antiperspirants and the like but can also be applied to the formulation of cosmetic makeup preparations such as eye shadows, mascaras, eyeliners and the like provided that the preparation is a water-base composition.

It is of course optional according to need that the hair-care and skin-care toiletry preparations prepared according to the inventive method are admixed, besides the ingredients inherent in the respective formulations of the base mixture of toiletry preparations and the aqueous dispersion of the cured silicone rubber particles, with various kinds of known adjuvants including astringents to reduce perspiration, germicides to prevent growth of microorganisms, shape-building oily excipients, volatile oily agents to impart a cool and refreshing feeling to the user after use of the toiletry preparation, fillers, ultraviolet absorbers, perfumes, moisturizers, preservatives, antioxidants, stabilizers and so on.

The actual procedure in step (b) of the inventive method for the preparation of the inventive water-base toiletry preparation, which can be batch-wise or continuous, is widely varied depending on the formulations and types of the respective preparations. The aqueous dispersion of cured silicone rubber particles can be admixed with the other ingredient or ingredients at any stage of the compounding procedure by using a blending machine which can be conventional including homomixers, homogenizers, propeller-blade mixers, in-line continuous emulsifiers and the like.

Despite the so wide diversity in the types and preparation forms of the water-base hair-care and skin-care toiletry preparations prepared according to the inventive method in which the cured silicone rubber particles are mixed with the other ingredients in the form of an aqueous dispersion, advantages are generally accomplished in respect of the smoothness and uniformity in the compounding of the cured silicone rubber particles to impart the toiletry preparations with reproducible improvements in the sleekness of touch feeling of the hair or skin after treatment with the toiletry preparation prepared according to the invention.

In the following, the method of the present invention is described in more detail by way of examples describing, first, preparation procedures of several aqueous dispersions of cured silicone rubber particles and then the formulations and compounding procedures of several water-base hair-care and skin-care toiletry preparations by using the aqueous dispersions of the cured silicone rubber particles as well as the results of the organoleptic evaluation tests thereof. In the following descriptions, the values of viscosity all refer to the values obtained by the measurements at 25° C. and the "%" fractions of the respective ingredients in the formulations of the toiletry preparations refer to "% by weight" fractions.

Preparation of silicone rubber particle dispersion-1

A uniform mixture consisting of 500 g of a vinyl-terminated dimethylpolysiloxane having a viscosity of 600 centistokes and expressed by the formula

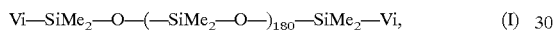

$$\text{Vi—SiMe}_2\text{—O—(—SiMe}_2\text{—O—)}_{180}\text{—SiMe}_2\text{—Vi,} \quad \text{(I)}$$

in which Me is a methyl group and Vi is a vinyl group, and 20 g of a methylhydrogenpolysiloxane having a viscosity of 30 centistokes and expressed by the formula

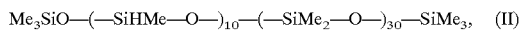

$$\text{Me}_3\text{SiO—(—SiHMe—O—)}_{10}\text{—(—SiMe}_2\text{—O—)}_{30}\text{—SiMe}_3, \quad \text{(II)}$$

was prepared in a glass beaker of 1 liter capacity by agitation with a homomixer rotating at 2000 rpm and the mixture was further admixed with 5 g of a polyoxyethylene (9 moles addition of ethylene oxide) octylphenyl ether as a non-ionic surface active agent and 150 g of water followed by continued agitation with the homomixer rotating at 6000 rpm so that a phenomenon of phase inversion took place from the initial water-in-oil emulsion to an oil-in-water emulsion with a noticeable increase in the viscosity. The oil-in-water emulsion was diluted with addition of 329 g of water under agitation with the homomixer rotating at 2000 rpm.

The above prepared oil-in-water emulsion was transferred into a glass flask equipped with an anchor-blade stirrer and, after further addition of a mixture of 1 g of the same surface active agent as used above and 1 g of a toluene solution of a chloroplatinic acid-olefin complex in a concentration of 0.05% by weight as platinum, was agitated at room temperature for 12 hours to effect the hydrosilation reaction between the vinyl groups in the vinyl-terminated dimethylpolysiloxane and the silicon-bonded hydrogen atoms in the methylhydrogenpolysiloxane so that the aqueous emulsion was converted into an aqueous dispersion of cured silicone rubber particles, referred to as the dispersion-1 hereinafter, of which the content of the cured silicone rubber particles was 52% by weight.

The thus obtained aqueous dispersion of cured silicone rubber particles was subjected to the measurement of the average particle diameter of the particles on a Coulter Counter (trade name of an instrument manufactured by Coulter Electronics Co.) to give a value of about 3 μm. A small portion of the dispersion-1 was taken on a dish and air-dried to give a white powder of which the particles exhibited rubbery elasticity and had a globular configuration as examined under an optical microscope.

Separately, another mixture of 500 g of the same vinyl-terminated dimethylpolysiloxane and 20 g of the same methylhydrogenpolysiloxane each as used above was admixed with 1 g of the same toluene solution of the chloroplatinic acid-olefin complex and the mixture taken in an aluminum dish of 60 mm inner diameter and 10 mm depth was kept standing at room temperature for 12 hours so that the liquid mixture was converted into a sheet of a cured silicone rubber having a thickness of about 8 mm, of which the rubber hardness was measured according to the procedure specified in JIS K 6301 by using a spring-type hardness tester A to give a value of 29.

Preparation of silicone rubber particle dispersion-2

A uniform mixture consisting of 280 g of a vinyl-terminated dimethylpolysiloxane having a viscosity of 10 centistokes and expressed by the formula

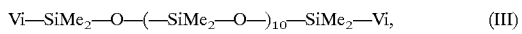

$$\text{Vi—SiMe}_2\text{—O—(—SiMe}_2\text{—O—)}_{10}\text{—SiMe}_2\text{—Vi,} \quad \text{(III)}$$

in which Me is a methyl group and Vi is a vinyl group, and 90 g of a methylhydrogenpolysiloxane having a viscosity of 200 centistokes and expressed by the formula

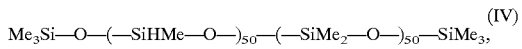

$$\text{Me}_3\text{Si—O—(—SiHMe—O—)}_{50}\text{—(—SiMe}_2\text{—O—)}_{50}\text{—SiMe}_3, \quad \text{(IV)}$$

was prepared in a glass beaker of 1 liter capacity by agitation with a homomixer rotating at 2000 rpm and the mixture was further admixed with 3 g of a polyoxyethylene (9 moles addition of ethylene oxide) octylphenyl ether as a non-ionic surface active agent and 70 g of water followed by continued agitation with the homomixer rotating at 6000 rpm so that a phenomenon of phase inversion took place from the initial water-in-oil emulsion to an oil-in-water emulsion with a noticeable increase in the viscosity. The oil-in-water emulsion was diluted with addition of 295 g of water under agitation with the homomixer rotating at 2000 rpm.

The above prepared oil-in-water emulsion was transferred into a glass flask equipped with a stirrer and, after further addition of a mixture of 1 g of the same surface active agent as used above and 1 g of a toluene solution of a chloroplatinic acid-olefin complex in a concentration of 0.05% by weight as platinum, was agitated at room temperature for 12 hours to effect the hydrosilation reaction between the vinyl groups of the vinyl-terminated dimethylpolysiloxane and the silicon-bonded hydrogen atoms in the methylhydrogenpolysiloxane so that the aqueous emulsion was converted into an aqueous dispersion of cured silicone rubber particles, referred to as the dispersion-2 hereinafter, of which the content of the cured silicone rubber particles was 50% by weight.

The thus obtained aqueous dispersion of cured silicone rubber particles was subjected to the measurement of the average particle diameter of the particles on a Coulter Counter (supra) to give a value of about 4 μm. A small portion of the dispersion-2 was taken on a dish and air-dried to give a white powder of which the particles exhibited rubbery elasticity and had a globular configuration as examined under an optical microscope.

Separately, another mixture of 280 g of the same vinyl-terminated dimethylpolysiloxane and 90 g of the same methylhydrogenpolysiloxane each as used above was admixed with 1 g of the same toluene solution of the chloroplatinic acid-olefin complex and the liquid mixture taken in an aluminum dish was converted in the same manner as described above into a sheet of a cured silicone rubber having a thickness of about 8 mm of which the rubber hardness was measured to give a value of 75 in the JIS A scale.

Preparation of silicone rubber particle dispersion-3

A uniform mixture consisting of 500 g of the vinyl-terminated dimethylpolysiloxane having a viscosity of 600 centistokes and expressed by the formula (I) and 20 g of the methylhydrogenpolysiloxane having a viscosity of 30 centistokes and expressed by the formula (II) was prepared in a glass beaker of 1 liter capacity by agitation with a homomixer rotating at 2000 rpm and the mixture was further admixed with 0.5 g of the polyoxyethylene (9 moles addition of ethylene oxide) octylphenyl ether as a non-ionic surface active agent and 479 g of water followed by continued agitation with the homomixer rotating at 6000 rpm so that a phenomenon of phase inversion took place from the initial water-in-oil emulsion to an oil-in-water emulsion.

The above prepared oil-in-water emulsion was transferred into a glass flask equipped with an anchor-blade stirrer and, after further addition of a mixture of 1 g of the same surface active agent as used above and 1 g of the same toluene solution of a chloroplatinic acid-olefin complex as used in the preparation of the dispersions-1 and -2, was agitated at room temperature for 12 hours to effect the hydrosilation reaction between the vinyl groups of the vinyl-terminated dimethylpolysiloxane and the silicon-bonded hydrogen atoms in the methylhydrogenpolysiloxane so that the aqueous emulsion was converted into an aqueous dispersion of cured silicone rubber particles, referred to as the dispersion-3 hereinafter, of which the content of the cured silicone rubber particles was 52% by weight.

The thus obtained aqueous dispersion of cured silicone rubber particles was subjected to the measurement of the average particle diameter of the particles on a Coulter Counter (supra) to give a value of about 120 µm. A small portion of the dispersion-3 was taken on a dish and air-dried to give a white powder of which the particles exhibited rubbery elasticity and had a globular configuration as examined under an optical microscope.

The hardness of the thus obtained silicone rubber particles was assumed to be 29, i.e. the same as in the dispersion-1, in the JIS A scale since the formulation relative to the vinyl-terminated dimethylpolysiloxane and methylhydrogenpolysiloxane and the reaction conditions were just the same as in the preparation of the dispersion-1.

EXAMPLE 1

(Hair Shampoo)

A water-base hair shampoo composition was prepared by uniformly blending, using a propeller-blade stirrer, following ingredients (1) to (7) at one time at room temperature.

| (1) Sodium polyoxyethylene (3 moles addition of ethylene oxide) laurylsulfate | 16% |
|---|---|
| (2) Laurylsulfuric acid diethanolamide | 4% |
| (3) 50% aqueous emulsion of dimethylpolysiloxane (5000 centistokes) | 3% |
| (4) Aqueous dispersion-1 | 1% |
| (5) Propyleneglycol | 2% |
| (6) Methyl p-hydroxybenzoate | 0.1% |
| (7) Purified water | balance |
| Total | 100% |

The thus prepared hair shampoo composition was used by a panel member for shampooing of her hair and, after drying with a hot-air blower, a combing test of the thus finished dry hair was undertaken to find that combing could be performed very smoothly with little resistance. The touch feeling of the finished hair was excellently dry and innocent of oiliness.

EXAMPLE 2

(Hair Rinse Composition)

A water-base hair rinse composition was prepared in the following formulation from the ingredients (1) to (8) in the manner described below.

| (1) Stearyl trimethyl ammonium chloride | 1% |
|---|---|
| (2) Cetanol | 2% |
| (3) 50% aqueous emulsion of dimethylpolysiloxane (5000 centistokes) | 4% |
| (4) Aqueous dispersion-2 | 2% |
| (5) Propyleneglycol | 5% |
| (6) Hydroxyethyl cellulose | 1% |
| (7) Methyl p-hydroxybenzoate | 0.1% |
| (8) Purified water | balance |
| Total | 100% |

Thus, the ingredients (6) and (8) were heated together at 70° C. to give a solution which was admixed under agitation with a mixture of the ingredients (1), (2) and (5) prepared separately by heating them together at 70° C. After cooling down to 50° C., the mixture was admixed with the ingredients (3), (4) and (7) followed by further cooling under agitation down to room temperature to give a water-base hair rinse composition.

After shampooing with a conventional commercial product of a hair shampoo composition, the hair of a panel member was treated on the surface with the thus prepared hair rinse composition followed by gentle rinse with water and drying by using a hot-air blower. A combing test of the thus finished dry hair was undertaken to find that combing could be performed very smoothly with little resistance. The touch feeling of the finished hair was excellently dry and innocent of oiliness.

EXAMPLE 3

(Emollient Cream Composition)

A water-base emollient cream composition was prepared in the following formulation from the ingredients (1) to (8) in the manner described below.

| (1) Stearic acid | 14% |
|---|---|
| (2) Petrolatum | 2% |
| (3) Aqueous dispersion-1 | 5% |
| (4) Self-emulsifiable glycerin monostearate | 2% |
| (5) Polyoxyethylene (20 moles ethylene oxide addition) sorbitan monostearate | 1% |
| (6) Methyl p-hydroxybenzoate | 0.1% |
| (7) Propyleneglycol | 10% |
| (8) Purified water | balance |
| Total | 100% |

Thus, the ingredients (7) and (8) were mixed under heating at 70° C. to give a uniform solution as the aqueous phase which was gradually admixed under agitation with a mixture of the ingredients (1), (2), (4) and (5) prepared separately by heating at 70° C. The mixture was agitated by using a homomixer to give an emulsion which was, after cooling down to 45° C., admixed with the ingredients (3)

and (6) followed by further cooling to room temperature to give a water-base emollient cream composition.

The emollient cream composition was applied to and spread over the face skin of a panel member after face washing by using a conventional soap and the emollient cream was gently wiped off with a soft cloth. The thus treated face skin was inspected by a finger touch test to find that the skin exhibited a very excellent dampish and slippery touch feeling.

EXAMPLE 4

(Emollient Lotion)

A water-base emollient lotion was prepared in the following formulation from the ingredients (1) to (12) in the manner described below.

| | | |
|---|---|---|
| (1) | Squalane | 5% |
| (2) | Petrolatum | 2% |
| (3) | Beeswax | 0.5% |
| (4) | Aqueous dispersion-2 | 3% |
| (5) | Sorbitan sesquioleate | 0.8% |
| (6) | Polyoxyethylene (20 moles ethylene oxide addition) oleyl ether | 1% |
| (7) | Propyleneglycol | 5% |
| (8) | Ethanol | 5% |
| (9) | Carboxyvinyl polymer (1% aqueous solution) | 20% |
| (10) | Potassium hydroxide | 0.1% |
| (11) | Methyl p-hydroxybenzoate | 0.1% |
| (12) | Purified water | balance |
| | Total | 100% |

Thus, the ingredients (7), (8) and (12) were mixed together to form an aqueous medium which was admixed at 70° C. under agitation with a uniform mixture of the ingredients (1), (2), (3), (5) and (6) prepared separately and kept at 70° C. The mixture was further admixed with the ingredient (9) and then with the ingredient (10) followed by emulsification by using a homomixer to give a uniform aqueous emulsion which was, after cooling down to 45° C., admixed with the ingredients (4) and (11) under agitation and cooled to room temperature to give a water-base emollient lotion.

The water-base emollient lotion prepared in the above described manner was applied to and spread over the face skin of a panel member after face washing by using a conventional soap and the lotion was gently wiped off with a soft cloth. The thus treated face skin was inspected by a finger touch test to find that the skin exhibited a very excellent dampish and slippery touch feeling.

COMPARATIVE EXAMPLE 1

A comparative water-base hair shampoo composition was prepared in the same formulation and procedure as in Example 1 described above excepting for the omission of the aqueous dispersion-1. The results of the hair shampooing test with this comparative shampoo composition for the combing behavior and touch feeling were that the shampooed hair was clearly inferior in the slipperiness and dry touch feeling as compared with the hair in Example 1.

COMPARATIVE EXAMPLE 2

A comparative water-base hair rinse composition was prepared in the same formulation and procedure as in Example 2 described above excepting for the omission of the aqueous dispersion-2. The results of the hair rinse test with this comparative hair rinse composition for the combing behavior and touch feeling were clearly inferior as compared with the hair in Example 2.

COMPARATIVE EXAMPLE 3

A comparative water-base emollient cream composition was prepared in the same formulation and procedure as in Example 3 described above excepting for the omission of the aqueous dispersion-1. The results of the face creaming test with this comparative emollient cream composition were that the treated face skin was clearly inferior in the touch feeling of sleekness and dampishness as compared with the face skin in Example 3.

COMPARATIVE EXAMPLE 4

A comparative water-base emollient lotion was prepared in the same formulation and procedure as in Example 4 described above excepting for the omission of the aqueous dispersion-2. The results of the touch feeling test of the face skin treated with this comparative emollient lotion were that the treated face skin was clearly inferior in the touch feeling of sleekness and dampishness as compared with the face skin in Example 4.

COMPARATIVE EXAMPLE 5

Another comparative water-base hair shampoo composition was prepared in the same formulation and procedure as in Example 1 described above excepting for the replacement of the aqueous dispersions with the same amount of the aqueous dispersion-3 having a coarser particle size distribution. The results of the hair shampooing test with this comparative shampoo composition for the combing behavior and touch feeling were that the shampooed hair was clearly inferior in the slipperiness of the hair with somewhat rough touch feeling as compared with the hair in Example 1.

COMPARATIVE EXAMPLE 6

Preparation of a comparative water-base hair shampoo composition was attempted in the same formulation and procedure as in Example 1 described above excepting for the replacement of 1% of the aqueous dispersion-1 with 0.5% of spherical silicone rubber particles obtained from the aqueous dispersion-1 by spray drying which, however, were floating in the upper layer of the liquid composition and could hardly be dispersed uniformly therein. The results of the evaluation test of the hair shampooed with this comparative hair shampoo composition were clearly inferior as compared with the hair in Example 1 in the slipperiness and dry touch feeling of the shampooed hair.

COMPARATIVE EXAMPLE 7

A still further comparative hair shampoo composition was prepared in the same formulation and procedure as in Example 1 describer above excepting for the replacement of 1% of the aqueous dispersion-1 with 0.5% of spherical particles of a polymethyl silsesquioxane resin assumedly having a hardness higher than 90 in the JIS A scale and an average particle diameter of about 3 $\mu$m. The results of the hair shampooing test with this comparative hair shampoo composition for the combing behavior and touch feeling were that the shampooed hair was clearly inferior in the slipperiness of the hair with somewhat rough touch feeling as compared with the hair in Example 1.

What is claimed is:

1. A method for the preparation of a water-base toiletry preparation which comprises the steps of:

(a) preparing an aqueous dispersion of spherical particles of a cured silicone rubber having an average particle diameter in the range from 0.1 to 100 μm dispersed in an aqueous medium containing a surface active agent, the amount of the cured silicone rubber particles being in the range from 1 to 70% by weight, the amount of the surface active agent being in the range from 0.1 to 20% by weight and the balance being water, each based on the amount of the aqueous dispersion; and (b) admixing a base mixture of a water-base toiletry preparation with the aqueous dispersion of the cured silicone rubber particles prepared in step (a) in such a proportion that the content of the cured silicone rubber particles in the toiletry preparation is in the range from 0.1 to 30% by weight based on the total amount of the non-volatile matters in the base mixture.

2. The method for the preparation of a water-base toiletry preparation as claimed in claim 1 in which the aqueous dispersion of cured silicone rubber particles is prepared in step (a) by the method of in situ crosslinking reaction in a mixture consisting of an alkenyl group-containing diorganopolysiloxane and an organohydrogenpolysiloxane jointly emulsified in an aqueous medium containing a surface active agent by the mechanism of the hydrosilation reaction between the alkenyl groups in the alkenyl group-containing diorganopolysiloxane and the silicon-bonded hydrogen atoms in the organohydrogenpolysiloxane in the presence of a platinum compound as a catalyst for the hydrosilation reaction.

3. The method for the preparation of a water-base toiletry preparation as claimed in claim 1 in which the content of the cured silicone rubber particles in the toiletry preparation is in the range from 1 to 10% by weight based on the total amount of the non-volatile matters in the base mixture.

4. The method for the preparation of a water-base toiletry preparation as claimed in claim 1 in which the surface active agent used in step (a) is a non-ionic surface active agent.

5. The method for the preparation of a water-base toiletry preparation as claimed in claim 1 in which the spherical particles of a cured silicone rubber in the aqueous dispersion prepared in step (a) have an average particle diameter in the range from 1 to 10 μm.

6. The method for the preparation of a water-base toiletry preparation as claimed in claim 2 in which the alkenyl group-containing diorganopolysiloxane is a vinyl group-containing dimethylpolysiloxane.

7. The method for the preparation of a water-base toiletry preparation as claimed in claim 2 in which the organohydrogenpolysiloxane is a methylhydrogenpolysiloxane.

* * * * *